United States Patent [19]

Ishikawa

[11] 4,435,176

[45] Mar. 6, 1984

[54] NEEDLE ASSEMBLY

[76] Inventor: Soji Ishikawa, No. 6-22, Miyazaki 6-chome, Takatsu-ku, Kawasaki-shi, Kanagawa-ken, Japan

[21] Appl. No.: 347,160

[22] Filed: Feb. 9, 1982

[30] Foreign Application Priority Data

Oct. 22, 1981 [JP] Japan .............................. 56-156380[U]

[51] Int. Cl.³ .............................................. A61M 5/32
[52] U.S. Cl. ..................................... 604/190; 604/240
[58] Field of Search ............... 604/188, 190, 206, 239, 604/240

[56] References Cited

U.S. PATENT DOCUMENTS 3,096,763  7/1963  McConnaughey et al. ......... 604/240
4,061,143  12/1977  Ishikawa ............................. 604/190
4,137,917  2/1979  Cohen ................................. 604/190

Primary Examiner—Stephen C. Pellegrino
Attorney, Agent, or Firm—Armstrong, Nikaido, Marmelstein & Kubovcik

[57] ABSTRACT

A needle assembly for use with a hypodermic syringe having a snout, which comprises a needle, a needle holder having a flare bore section for coupling with the snout of the syringe and a hollow pipe provided in the flared bore section of the needle holder. The pipe is shaped and sized to be inserted in a snout hole when the needle holder couples with the snout through the flared bore section formed therein. The pipe has a passage which communicates with a needle bore through a narrow hole formed in the needle holder. A filter may be provided in the needle holder. The quantity of liquid medicine left in the needle holder and the snout hole of the syringe after the injection is made extremely small. When the filter is provided in the needle holder, impurities can be removed.

3 Claims, 4 Drawing Figures

NEEDLE ASSEMBLY

BACKGROUND OF THE INVENTION

1. Field of the Invention

The present invention generally relates to a needle assembly for a hypodermic syringe, and more particularly to a needle assembly for a hypodermic syringe wherein the quantity of liquid medicine left in a needle holder and a snout hole of a syringe when the injection has been completed, is made extremely small.

2. Description of the Prior Art

In general, a needle assembly for a hypodermic syringe comprises a pointed needle and a needle holder which receives the needle at its one end. The needle holder is a hollow tubular member and is made flared from the needle receiving section towards its opposite open end so as to form a flared bore therein. This bore is shaped and sized to be tightly fitted over an externally tapered snout of a syringe in a manner so-called Leur taper coupling. In order to ensure the more tight gripping of the needle holder and the snout, it is necessary to leave a room in the bore between the free end of the tapered snout and the innermost end wall of the bore for allowing the snout to be further pushed forward if desired, even when the needle holder has been press fitted on the snout.

In the prior needle assembly, however, since a space including the room in the bore of the needle holder is left free and a snout hole of the syringe is left free also, there is a disadvantage that some extent of liquid medicine remains in the needle holder and in the snout hole, even when a plunger has been pressed to the maximum against the end wall of the syringe bore so as to force the liquid medicine completely out of the syringe bore. Such loss of the remaining liquid medicine can not be ignored and is worth due consideration, particularly when the liquid medicine is an expensive one, such as insulin etc. Further, there is another disadvantage in the prior art needle assembly that impurities enter in the liquid medicine in the syringe bore and are consequently introduced in a human body, particularly when insulin is used wherein a patient himself is legally permitted to inject the same into his body. These impurities include not only a dust or fine particles floating in the air, but also fine fragments of glass which are produced when an ampoule is cut away.

SUMMARY OF THE INVENTION

Therefore, an object of the present invention is to provide an improved needle assembly for a hypodermic syringe wherein vacant space in a needle holder and a snout hole of a syringe is minimized, so that the quantity of liquid medicine left there, is made extremely small after the injection of the medicine into the body has been finished.

Another object of the present invention is to provide an improved needle assembly which can remove impurities from the liquid medicine.

In accordance with the present invention, there is provided a needle assembly for use with a hypodermic syringe having a snout, which comprises a needle, a needle holder having a flared bore section for coupling with the snout of the syringe and a hollow pipe provided in the flared bore section of the needle holder. The pipe is shaped and sized to be inserted in a snout hole when the needle holder couples with the snout through the flared bore section formed therein. The pipe has a passage which communicates with a needle bore through a narrow hole in the needle holder. A filter may be provided in the needle holder.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and in which.

DESCRIPTION OF THE PREFERRED EMBODIMENTS

Figure 1:
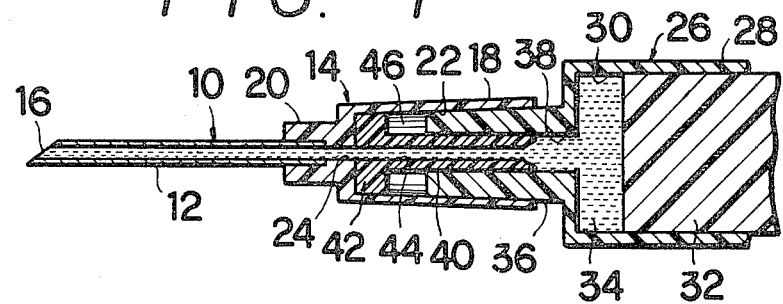
FIG. 1 is an enlarged cross sectional view showing a needle assembly in accordance with the present invention.

Referring now to the drawings and FIG. 1 in particular, there is shown a needle assembly 10 for a hypodermic syringe according to the present invention, which comprises a needle 12 and a needle holder 14. The needle 12 has a piercing point at its free end and is partially embedded in an end of the needle holder 14 at the other end. In the needle 12, there is formed an axial bore 16 which extends throughout the length. The needle holder 14 comprises a generally tubular body portion 18 and a tip portion 20, which are integrally connected together. The tip portion 20 receives the end of the needle 12 as explained before.

The tubular body portion 18 of the needle holder 14 is made flared towards its open end from the inner end of the tip portion 20. The thickness of a wall of the tubular body portion 18 is kept equal throughout the length, so that there is formed a flared bore 22 in the tubular body portion 18 of the needle holder 14.

The tip portion 20 has a narrow hole 24 therein which communicates with the flared bore 22 of the tubular body portion 18 and in turn, meets with an end of the needle bore 16, so that the flared bore 22 communicates with the needle bore 16 through the narrow hole 24.

Reference numeral 26 indicates a well-known hypodermic syringe which includes a syringe barrel 28 having a longitudinal bore 30 therein and a plunger 32 longitudinally slidable in the bore 30 for forcing the liquid medicine 34 in the bore or out therefrom. The syringe barrel 28 has, at its leading end, a snout 36 which is tapered towards its tip end. Thus, the flared bore 22 of the needle holder 14 can be press fitted over the tapered snout 36 of the syringe barrel 28 and tightly engaged thereon, in a manner so-called Leur taper coupling.

The snout 36 has a hole 38 which communicates with the syringe bore 30, so that after the needle holder has been fitted on the snout 36, there is formed a passageway from the syringe bore 30 to the piercing point of the needle via the flared bore 22 and the narrow hole 24, where the liquid medicine 34 in the syringe bore 30 flows by.

In the flared bore 22 of the needle holder 14, there is provided a hollow small pipe 40. The small pipe 40 is expanded radially, at the innermost end thereof, perpendicular to its longitudinal axis, so as to form a bulged portion 42 which is fixed at the innermost cylindrical wall of the flared bore 22 by means of an appropriate means such as a high-frequency welding. Thus, the small pipe 40 is fixed in the flared bore by means of the bulged portion 42 so as to protrude towards the flared open end in such a manner that it can be inserted in the snout hole 36 when the needle holder 14 engages with the snout 32 of the syringe 26. The small pipe has a central hole 44 therein which extends throughout its length and in alignment with the narrow hole 24 of the tip portion 20 and in further alignment with the needle bore 16. Thus, there is formed a passage from the syringe bore 30 to the piercing point of the needle 12 through the pipe hole 44.

It is important that there should be still left a room 46 between the outer end of the bulged portion 42 of the pipe 40 and the tapered end of the snout 36 in the flared bore. Said room 46 allows the snout 36 to be further pushed forward in order to ensure the more tightly gripping of the needle holder 14 and the snout 36, even when the needle holder has been press fitted on the snout through its flared bore 22. However, it is needless to say that the liquid medicine 34 does no longer remain in the room 46 after the injection, since the room 46 is kept out of the liquid passage and the liquid medicine does no longer enter therein. Thus, as the room 46 is left out of the liquid passage, and since the bore 22 as well as the snout hole 38 is occupied by the pipe 40, the quantity of the liquid medicine 34 left in the snout hole and the needle holder after the injection becomes extremely small.

The small pipe 40 shown in the embodiment is a straight pipe having an equal diameter throughout its length, except for the bulged portion 42, corresponding to the shape of the inner wall of the snout hole 38 which is made straight also. However the pipe may be tapered towards its free end if the inner wall of the snout hole is flared towards its tip end. In any case, the pipe should be shaped and sized to tightly fit with the inner wall of the snout hole when the needle holder couples with the snout of the syringe barrel.

Figure 2:
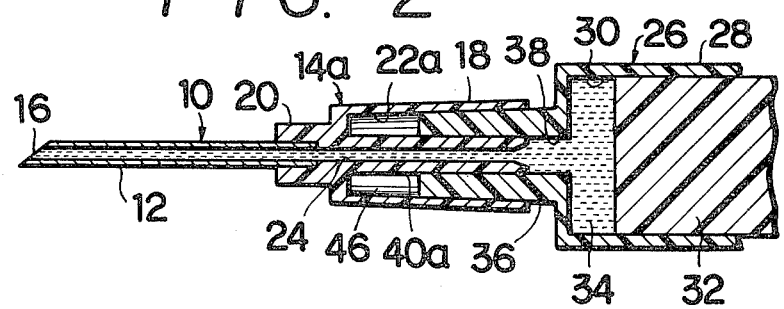
FIG. 2 is similar to FIG. 1 but shows another embodiment of the present invention.

FIG. 2 shows a modified embodiment of the needle assembly, wherein a small pipe 40a is integrally formed with the needle holder 14a such that the small pipe 40a protrudes from the innermost end wall of the flared bore 22a of the needle holder 14a.

Figure 3:
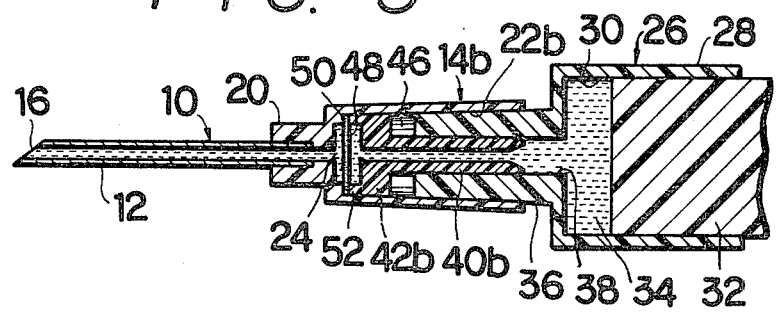
FIG. 3 is an enlarged cross-sectional view showing a further embodiment of the present invention.
Figure 4:
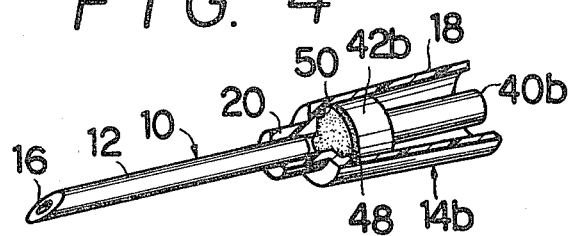
FIG. 4 is a perspective view, partially broken away, of the needle assembly of FIG. 3.

FIGS. 3 and 4 show a further modified embodiment of the needle assembly, wherein there is further provided a filter 48 which is fixed between the innermost end wall of the flared bore 22b and the bulged portion 42b of the small pipe 40b. The filter 48 is a plate-like filter and carried by an annular step 50 formed on the circumferential edge of the end wall of the flared bore 22b and an annular projection 52 formed on the circumferential edge of the inner wall of the bulged portion 42b of the pipe 40b. With this arrangement, the filterability can be improved, since the filter 48 is operable substantially throughout its area except for the area contacting with the annular projections 50,52. The filter 48 can remove impurities from the liquid medicine.

Various kinds of filters including not only a plate-like filter such as a membrane filter or a sintered plastics filter but also any other filter such as a filter made of a pile of fibers or hollow fibers, can be provided at the area which communicates with the needle bore and, in turn communicates with the small pipe in the needle holder 14b. In any case, a filter should be fixed there in an appropriate manner according to the type of the filter.

Having described as above, after the needle holder has been press fitted over the snout while inserting the small pipe in the snout hole, liquid medicine forced out from the syringe bore can be immediately led to the needle through the small pipe during the injection, so that the quantity of the liquid medicine left in the snout hole and the needle holder can be made extremely small. Therefore, even when liquid medicine is expensive one such as insulin, the quantity of the remaining liquid will be immaterial.

Further, when the filter is mounted in the needle holder, the impurities can be perfectly removed out. And the injection can be done in a germ-free condition by selecting the pore size of the filter.

While the above description discloses preferred embodiments of the present invention, it is to be understood that numerous modifications or alterations may be made without departing from the scope of the invention as set forth in the following claims.

What is claimed is:

1. A needle assembly for use with a hypodermic syringe including a syringe barrel with a snout formed at its leading end, said snout being tapered towards its tip end and having a hole therein, which comprises:
   a needle having a longitudinal bore extending throughout its length;
   a needle holder receiving the needle at its one end and having a flared bore therein at its other end, said flared bore being shaped and sized to be press fitted over the tapered snout of the syringe barrel, said needle holder having a narrow hole in the needle receiving section which communicates with the flared bore;
   a hollow pipe fixed in the flared bore at the innermost area thereof by means of a bulged portion formed at a base thereof, said pipe being shaped and sized to be inserted in the snout hold and having a passage which communicates with the needle bore through the narrow hole in the needle holder; and
   a plate-like filter provided at the area in the needle holder which communicates with the needle and the pipe, the filter being carried by annular projections formed on the end walls of the pipe and the flared bore of the needle holder.

2. A needle assembly for use with a hypodermic syringe including a syringe barrel with a snout formed at its leading end, said snout being tapered towards its tip end and having a hole therein, which comprises:
   a needle having a longitudinal bore extending throughout its length;
   a needle holder receiving the needle at its one end and having a flared bore therein at its other end, said flared bore being shaped and sized to be press fitted over the tapered snout of the syringe barrel, said needle holder having a narrow hole in the needle receiving section which communicates with the flared bore;
   a hollow pipe fixed in the flared bore at the innermost area thereof by means of a bulged portion formed at a base thereof, said pipe being shaped and sized to be inserted in the snout hole and having a passage which communicates with the needle bore through the narrow hole in the needle holder, the bulged portion being shaped and sized to define an empty space between an outer end thereof and the tapered end of the snout.

3. A needle assembly as defined in claim 2, wherein a filter is provided at the area in the needle holder which communicates with the needle and the small pipe.

* * * * *